US012797229B2

(12) United States Patent
Montross

(10) Patent No.: US 12,797,229 B2
(45) Date of Patent: Nov. 17, 2026

(54) LEG AND/OR EXTREMITY SUPPORT

(71) Applicant: William Montross, Colorado Springs, CO (US)

(72) Inventor: William Montross, Colorado Springs, CO (US)

(*) Notice: Subject to any disclaimer, the term of this patent is extended or adjusted under 35 U.S.C. 154(b) by 63 days.

(21) Appl. No.: 18/427,684

(22) Filed: Jan. 30, 2024

(65) Prior Publication Data

US 2024/0252341 A1 Aug. 1, 2024

Related U.S. Application Data

(60) Provisional application No. 63/441,910, filed on Jan. 30, 2023.

(51) Int. Cl.
*A61F 5/37* (2006.01)
*A61B 17/62* (2006.01)

(52) U.S. Cl.
CPC ............ *A61F 5/3761* (2013.01); *A61B 17/62* (2013.01)

(58) Field of Classification Search
CPC .... A61F 5/3761; A61F 5/0585; A61F 5/0116; A61F 5/0111; A61B 17/62; A61B 17/66; A61B 17/6433; A61B 17/6441
See application file for complete search history.

(56) References Cited

U.S. PATENT DOCUMENTS 3,419,002 A * 12/1968 Santosus ............... A61F 5/0585 602/23
4,848,326 A * 7/1989 Lonardo ............... A61F 5/0585 602/26
2008/0200856 A1* 8/2008 Cadichon .............. A61F 5/0123 602/26

* cited by examiner

*Primary Examiner* — Ophelia A Hawthorne
(74) *Attorney, Agent, or Firm* — BRAINSPARK ASSOCIATES, LLC

(57) ABSTRACT

Disclosed are devices for positioning and supporting a leg or other patient extremity within an external support structure or frame.

10 Claims, 5 Drawing Sheets

LEG AND/OR EXTREMITY SUPPORT

CROSS-REFERENCE TO RELATED APPLICATIONS

This application claims priority to and benefit thereof from U.S. Provisional Patent Application No. 63/441,910, filed Jan. 30, 2023, entitled "LEG AND EXTREMITY HOLDER," the disclosure of which is hereby incorporated herein by reference in its entirety.

TECHNICAL FIELD

The invention relates to improved devices, systems and methods for positioning and supporting an appendage such as a leg or other patient extremity within an external support structure or frame.

BACKGROUND OF THE INVENTION

External fixators are often used as a method of immobilizing leg and other limb bones to allow a fracture to heal. These devices typically utilize pins or screws that are placed into the bone on all sides of the fracture. The pins and screws are then secured together outside the skin with clamps and rods within an external skeletal frame. As the bones mend back together, the external fixator can desirably be adjusted such that the bones remain in an optimal position during the healing process. While fixators perform their intended function very well, such devices are difficult to install, adjust, and remove while the bone mending process is being conducted or has been completed, and it is often necessary to access various locations of the limb during the healing process-including areas that may be occluded and/or shielded by various elements of the fixator. If such access is desired, it may be necessary for two or more people to support a user's appendage while another individual installs, adjusts, and/or removes various pins and/or screw components, as well as various other frame elements. Frequently, a leg or other extremity can shift posterior, anterior, medial and/or lateral relative to a frame structure, presenting a non-ideal position within the frame and/or causing the frame to rub on the extremity. Furthermore, removing frame portions can remove support and/or affect stabilization of the extremity, causing injury to the patient, and the patient is often extremely uncomfortable due to adverse pressure and/or stresses placed upon the appendage, as well as the difficulty of holding the appendage in place in an elevated position for a long period of time.

Traditionally, a leg can be held in position within a surgical support structure or frame by folded and stuffing towels or other items under the leg. Unfortunately, this can lead to poor positioning if the leg is moved and can also cause irritation of a damaged area that is being fixated as well as soft tissue injury from the supporting structures and/or holder to the patient. While some companies have proposed using plastic blocks or similar support structures, such devices are bulky, are difficult to use, place and remove, and can often provide uneven support and even cause additional damage such as pressure sores or the like, especially for obese patients or those suffering from circulatory disorders. Thus, there is a need in the art for improved devices, systems and methods for positioning and supporting a leg or other patient extremity within an external support structure or frame.

BRIEF SUMMARY OF THE INVENTION

The present invention includes the realization of a need in the art for improved devices, systems and methods for positioning and supporting a leg or other patient extremity within an external support structure or frame. In various embodiments, the devices and systems disclosed herein can facilitate the positioning, placement and/or orientation/re-orientation of an arm or other extremity within a support frame, such as in an external fixation frame, providing uniform and comfortable support for the patient for an extended period of time, when necessary. In addition, the device can desirably be easily repositioned and/or removed at any point during a surgical procedure, at which time the device can be disposed or and/or reprocessed as desired.

The apparatus of the present invention is an aid to assist in the installation, adjustment, treatment and/or removal of an external fixator that has been placed on patient's leg or other extremity/limb. The apparatus includes an adjustable flexible support which can form a holding cradle or similar support for supporting a user's appendage in an elevated position within the frame. In a fixator removal situation for example, the apparatus can be positioned within a frame and then the frame and apparatus can be slid along the user's appendage. Desirably, the apparatus provides support for the user's appendage while supporting the appendage within the fixator in an elevated position. The apparatus can be adjustable in height, width, positioning and/or length, and can be adjusted in a variety of ways to accommodate extremity support.

BRIEF DESCRIPTION OF THE SEVERAL VIEWS OF THE DRAWINGS

The foregoing and other features and advantages of the present subject matter will become apparent to those skilled in the art to which the present subject matter relates upon reading the following description with reference to the accompanying drawings.

FIG. 2 depicts exemplary support pins and locking devices which can be used to anchor an extremity support;

DETAILED DESCRIPTION OF THE INVENTION

Figure 1:
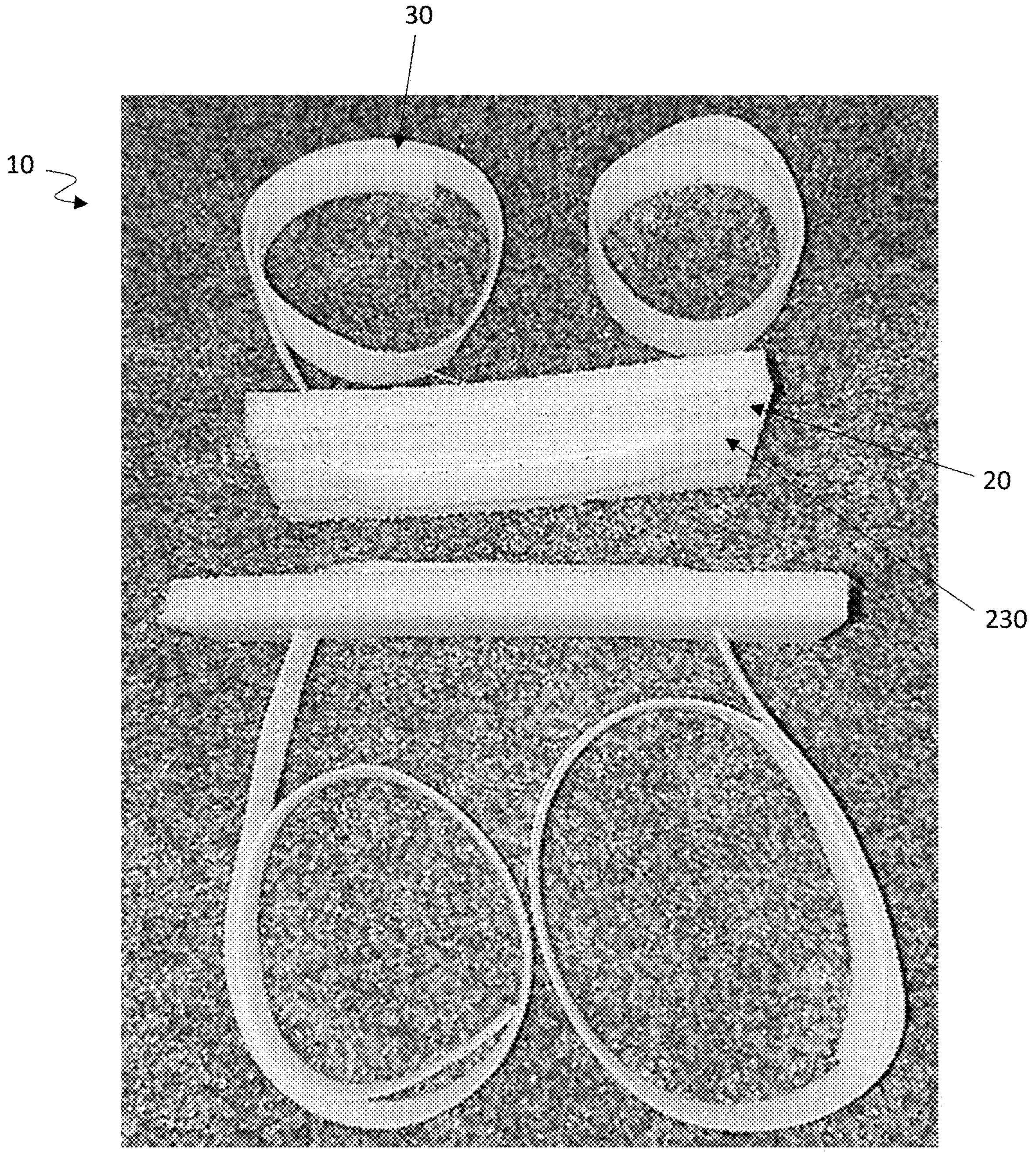
FIG. 1 depicts one exemplary embodiment of a pair of extremity supports constructed in accordance with various teaching of the present invention.

The present subject matter relates generally to devices for the fixation and support of extremities. In particular, the present subject matter relates to an adjustable extremity support device which can be used to quickly and conveniently support an extremity within a fixation frame for a variety of reasons.

The best mode for carrying out the invention is desirably presented in terms of its preferred embodiment. However, the invention is not limited to the described embodiment(s), and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

Desirably, the disclosed devices are highly adjustable and can allow a single individual to attach and/or otherwise support the patient's extremity for a variety of reasons, including the placement and/or removal of other frame elements while the extremity remains fully supported within the frame. The apparatus desirably presents a low cost, low-profile configuration that does not interfere with the installation, adjustment, modification and/or removal process of the fixator. Desirably, the user's appendage will remain comfortably supported by the apparatus, while affording the performance of the work of installation, adjustment, and/or removal (and/or other treatments) to be conducted by a single individual. Moreover, the support pins and holder straps of the disclosed devices can be easily repositioned during the case, such as to accommodate the external fixator and the extremity.

In one exemplary embodiment, an extremity support or sling can comprise a padded strap designed to attach to the frame in many ways. Padding can be designed to protect the extremity while being held for application/removal/adjustment of the pins or wires in the extremity and/or external fixation device, as well as cleaning, debridement, assessment and/or other treatment of the extremity. The padding can come in different sizes and shapes to accommodate the area of the extremity being help. Depending upon application and/or frame design, the device can attach to the frame, and may desirably be capable of attaching to itself with Velcro fasteners or hooks, etc. The flexible straps may loop over the ring, strut, rod or braces that can be temporarily attached to the frame during positioning and hold leg or other extremity while the frame construct is attached to the leg. Desirably, this device is simple to attach the leg to the frame and to easily be removed without disruption of the body part(s) being worked on.

While the disclosed devices and system can be useful in a variety of situations, the present invention may be particular useful during procedures employing orthopedic fixation systems, assemblies, devices and related methods for reduction of a fractured bone of a patient.

The present invention describes a limb support apparatus 10 for an external fixation frame (e.g., external fixator) or other surgical apparatus, configured to provide an aid to assist in procedures associated with the application, removal, adjustment and/or other activities involving an external fixator upon a patient's injured limb. One basic configuration of the support apparatus 10 is depicted in FIG. 1, where the support apparatus 10 includes a flexible cushion or pad 20, having one or more straps 30 attached thereto. Desirably, the limb facing surface of the pad 20 will preferably comprise a soft foam or elastomer material for the comfort of the wearer, while having sufficient strength and thickness to support the extremity. In various embodiments, the strap 30 can include an adjustable attachment system such a hook and loop or Velcro fasteners, wherein one side of the strap includes a hook surface and the opposing surface of the strap includes the corresponding loop surface. In other embodiments, the strap may include virtually any type of belt or strap structure including conventional fastener means such as a buckle or retaining clip, an adhesive surface, or a roughened and/or "sticky" surface such used in commonly available devices such as ACE™ brand self-adhering bandages (commercially available from 3M Company of Maplewood, Minnesota USA). Other fastening and/or adjustment techniques may be incorporated and/or substituted by those of ordinary skill in the art.

Figure 2:
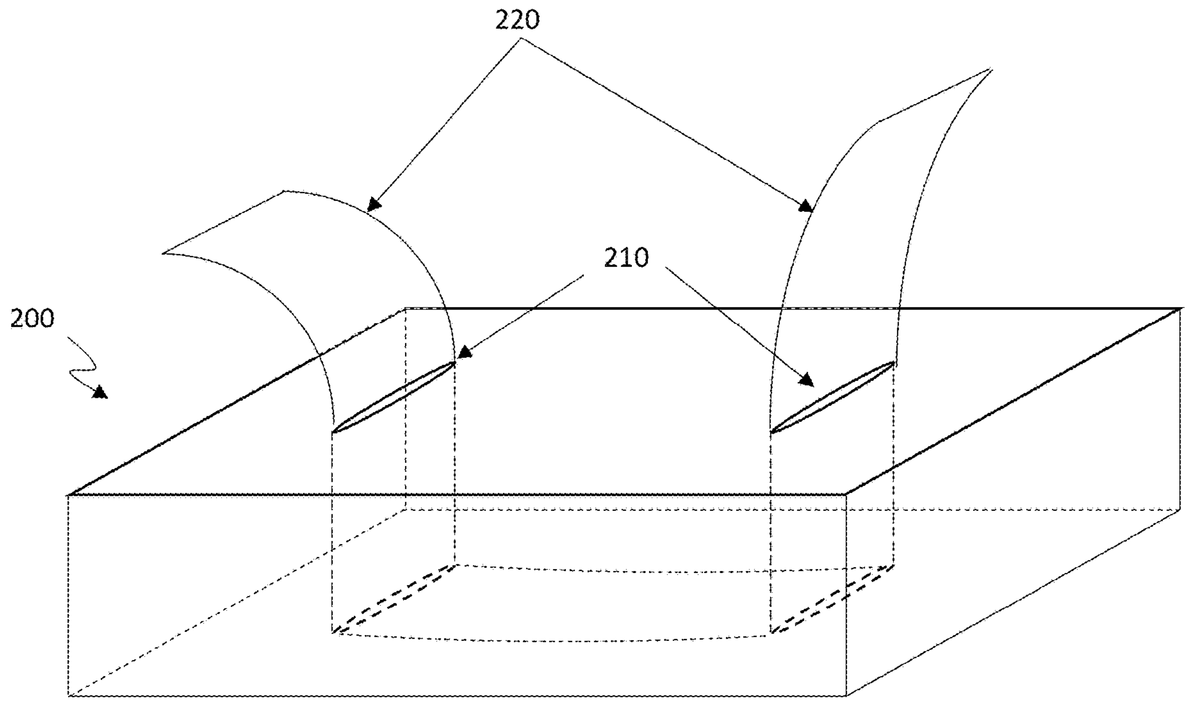
FIG. 2 is a side perspective view of a flexible cushion or pad for use with the extremity support of FIG. 1.
Figure 3A:
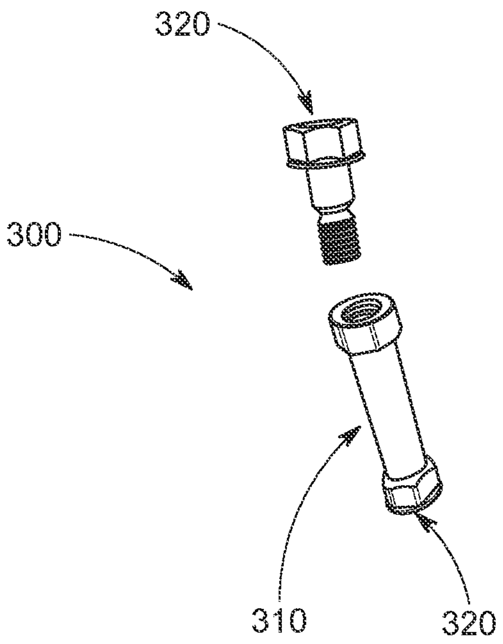
Figure 3B:
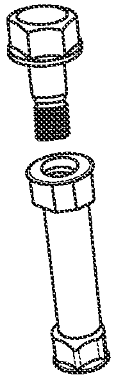
Figure 3C:
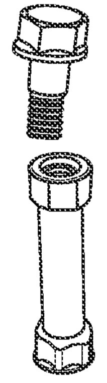
Figure 3D:

FIG. 2 depicts one exemplary embodiment of a flexible cushion or pad 200, wherein the pad includes one or more holes or openings 210 which allow a strap 220 to extend therethrough. In various embodiments, a strap section or cover 230 (see FIG. 1) can be secured to the pad in manner to cover over the strap yet allow the strap to slide relative to the pad 220 and/or openings therein.

FIG. 3 depicts a plurality of support pins 300 for use with the limb support apparatus of FIG. 1. Each support pin 300 can comprise a support body 310 and an anchor pin 320, wherein the anchor pin can be secured into a corresponding opening in the support body 310 (to sandwich a frame member therebetween). Desirably, an end 320 of the support body can include an enlarged portion, lip or flange 330, which can retain and/or prevent a strap from sliding off.

Figure 4:
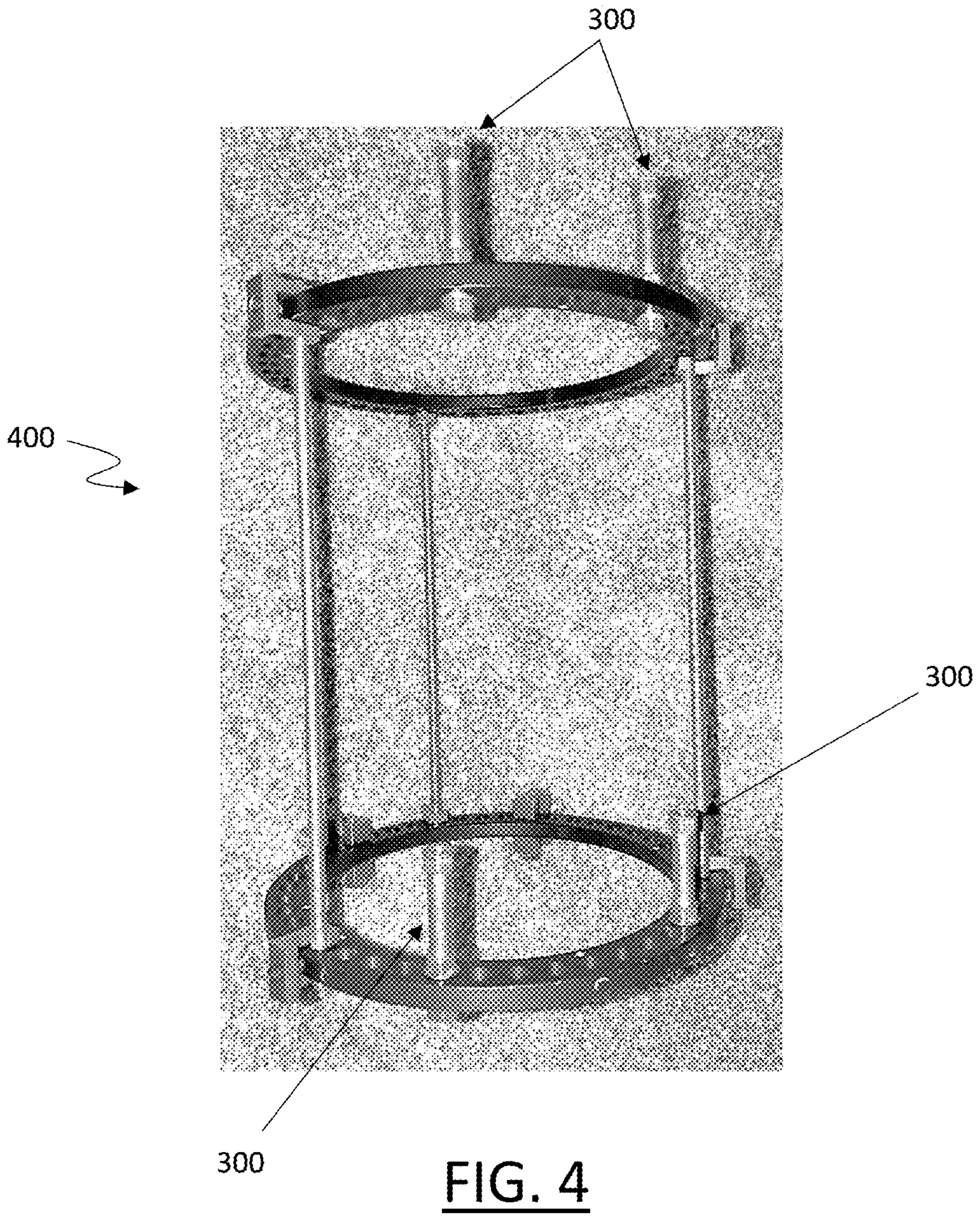
FIG. 4 depicts an exemplary fixation frame for use with the extremity support so FIG. 1.
Figure 5A:
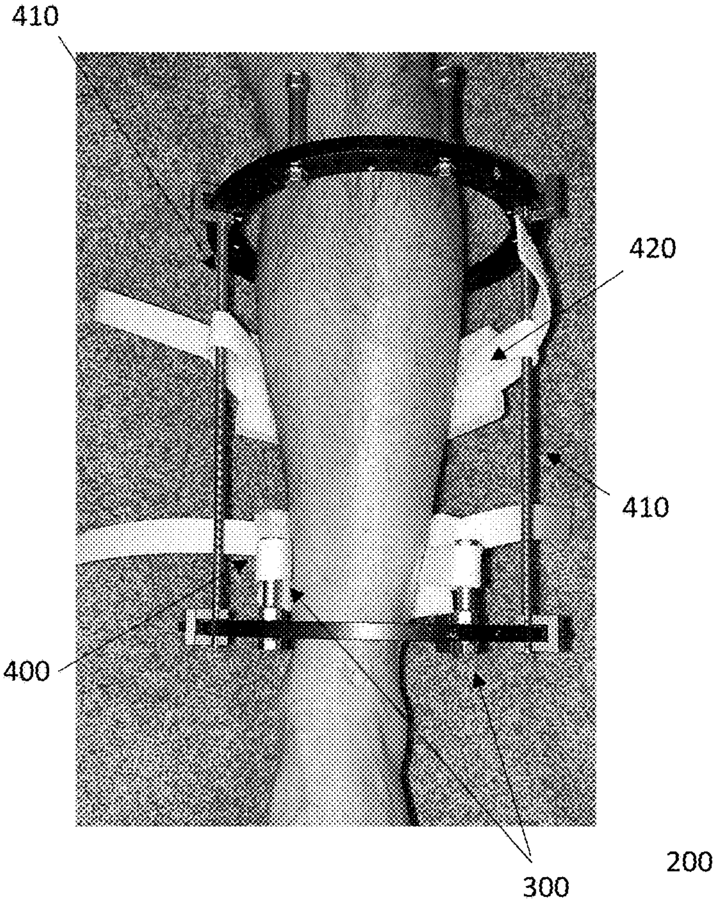
FIGS. 5A and 5B depict views of an extremity supported by an extremity support within an exemplary fixation frame.
Figure 5B:
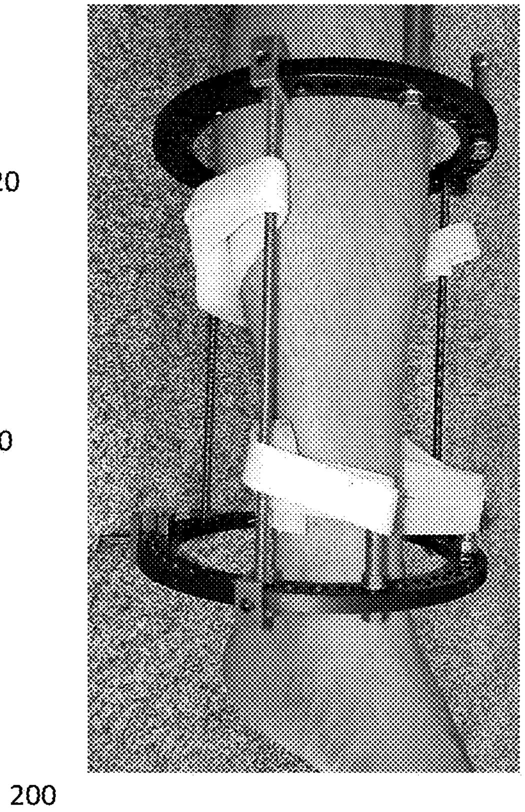

FIG. 4 depicts an exemplary fixation frame 400 wherein a plurality of support pins 300 are secured to the frame member (e.g., through an opening in a support arm, in a desired manner). As best seen in FIGS. 5A and 5B, a pair of support pins 300 can be utilized to secure a first limb support apparatus 400, and a second pair of frame elements or struts 410 can be utilized to support a second limb support apparatus 420. Desirably, the straps can be positioned and extend around the support pins and/or other frame components, including frame struts and/or ring members of the fixation frame on either side (e.g., dorsal or plantar) of the extremity. Desirably, the leg or other extremity can be positioned within the fixation frame, and the pad can contact the extremity with the Velcro straps secured to various support structures such as the described support pins and/or, if needed, they can be used on the rods/struts.

Desirably, the disclosed limb support apparatus provides support for the user's injured limb as long as necessary, is easy to apply and/or remove, is inexpensive, is optionally disposable and/or recyclable, may be sterilizable or otherwise reprocessed and/or reused, and is easy to reposition and/or reconfigure at the user's option, such as if the support interferes with a wire, a pin site and/or for any other reason. This apparatus is envisioned being available in various sizes and/or configurations for use on different sizes of limbs and/or portions of limbs, such as an upper leg, a lower leg, an ankle, an arm, a wrist, and the like. The support and positioning of the limb provided by the disclosed devices desirably reduces undesirable movement during installation, removal, adjustment and/or other manipulation of the fixator; enables removal of the fixator and/or adjustment thereof by one individual; and/or aids in the removal of pins, screws and/or other components associated with the fixator.

The specific dimensions of any of the systems, assemblies, and components thereof, of the present invention can be readily varied depending upon the intended application, as will be apparent to those of skill in the art in view of the disclosure herein. Moreover, it is understood that the examples and embodiments described herein are for illustrative purposes only and that various modifications or changes in light thereof may be suggested to persons skilled in the art and are included within the spirit and purview of this application and scope of the appended claims. Numerous different combinations of embodiments described herein are possible, and such combinations are considered part of the present invention. In addition, all features discussed in connection with any one embodiment herein can be readily adapted for use in other embodiments herein. The use of different terms or reference numerals for similar features in different embodiments does not necessarily imply differences other than those which may be expressly set forth. Accordingly, the present invention is intended to be described solely by reference to the appended claims, and not limited to the preferred embodiments disclosed herein.

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

GENERAL

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

The various headings and titles used herein are for the convenience of the reader, and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A device for supporting an extremity within an external fixation frame, comprising:

a central body comprising a flexible material having at least two openings formed therethrough, and a flexible strap extending through the at least two openings in the central body, the flexible strap including a first side having a hook-type connection surface and an opposing second side have a loop type connection surface, the flexible strap having a first end and an opposing second end, wherein the first end of the flexible strap is secured to a first location on the external fixation frame and the second end of the flexible strap is secured to a second location on the external fixation frame, wherein the first and second ends support the central body that is configured to be in intimate contact with the extremity.

2. The device of claim 1, wherein the extremity within the external fixation frame is a leg of a patient.

3. The device of claim 1, wherein the extremity within the external fixation frame is an arm of a patient.

4. The device of claim 1, wherein the flexible strap is configured not to directly contact the extremity.

5. The device of claim 1, wherein the extremity is configured not to come into direct contact with the fixation frame.

6. A device for supporting an extremity within an external fixation frame, comprising:

a central body comprising a flexible material having at least two openings formed therethrough, and a flexible strap extending through the at least two openings in the central body, the flexible strap including a first side having a hook-type connection surface and an opposing second side have a loop type connection surface, the flexible strap having a first end and an opposing second end, wherein the first end of the flexible strap is secured to a first location on the external fixation frame and the second end of the flexible strap is secured to a second location on the external fixation frame, wherein the first and second ends support the central body that is configured to be in intimate contact with the extremity and the central body is solely supported on the external fixation frame by the flexible strap.

7. The device of claim 6, wherein the extremity within the external fixation frame is a leg of a patient.

8. The device of claim 6, wherein the extremity within the external fixation frame is an arm of a patient.

9. The device of claim 6, wherein the flexible strap is configured not to directly contact the extremity.

10. The device of claim 6, wherein the extremity is configured not to come into direct contact with the fixation frame.

* * * * *